United States Patent [19]

Chang

[11] Patent Number: 4,830,441
[45] Date of Patent: May 16, 1989

[54] HOLOGRAPHIC FILTER CONSTRUCTION FOR PROTECTIVE EYEWEAR

[75] Inventor: B. Jin Chang, Ann Arbor, Mich.

[73] Assignee: Kaiser Optical Systems, Ann Arbor, Mich.

[21] Appl. No.: 30,720

[22] Filed: Mar. 25, 1987

[51] Int. Cl.[4] .............................................. G02B 5/32
[52] U.S. Cl. .................................... 350/3.7; 350/3.77
[58] Field of Search ................................ 350/3.7, 3.77

[56] References Cited

U.S. PATENT DOCUMENTS

| | | | |
|---|---|---|---|
| 3,867,009 | 2/1975 | Pawluczyk | 350/3.67 |
| 4,582,389 | 4/1986 | Wood et al. | 350/3.69 |
| 4,601,533 | 7/1986 | Moss | 350/3.7 |
| 4,637,678 | 1/1987 | Moss et al. | 350/3.7 |

OTHER PUBLICATIONS

Leith & Chang, "Space-Invariant Holography with Quasi-Coherent Light", Aug. 1973, pp. 1959–1963, Applied Optics, vol. 12, No. 8.

Magarinos and Coleman, "Holographic Mirrors", Sep.-/Oct. 1985, pp. 769–780, Optical Engineering, vol. 24, No. 5.

*Primary Examiner*—Bruce Y. Arnold
*Assistant Examiner*—Terry S. Callaghan
*Attorney, Agent, or Firm*—Krass & Young

[57] ABSTRACT

The present invention is a manner of constructing holographic optical elements for use in laser eye protection. A photosensitive layer, preferably formed of dichromated gelatin, is disposed on a transparent supporting substrate with a reflecting surface conformal to the outer surface of the photosensitive layer. The photosensitive layer is exposed with light from a laser point source. The photosensitive layer records the interference patterns between light incident directly from the laser point source and light reflected from the reflecting surface. The photosensitive layer is developed to form a holographic optical element. When this holographic optical element is disposed before the eye, with the center of the eye located at a point equivalent to the location of the laser point source, laser light directed toward the center of the eye is diffracted by the holographic optical element and effectively reflected away from the eye. Construction of the holographic optical element in this manner enables the use of a flatter spectacle lens while minimizing flare. The blocking angles at any particular portion of the holographic optical element can be reduced, thus increasing the transmissibility of the eyewear, without sacrificing protection. This technique also prevents the holographic optical element from being retroflective at all angles, thereby presenting a noncooperative target cross section to illuminating lasers.

49 Claims, 6 Drawing Sheets

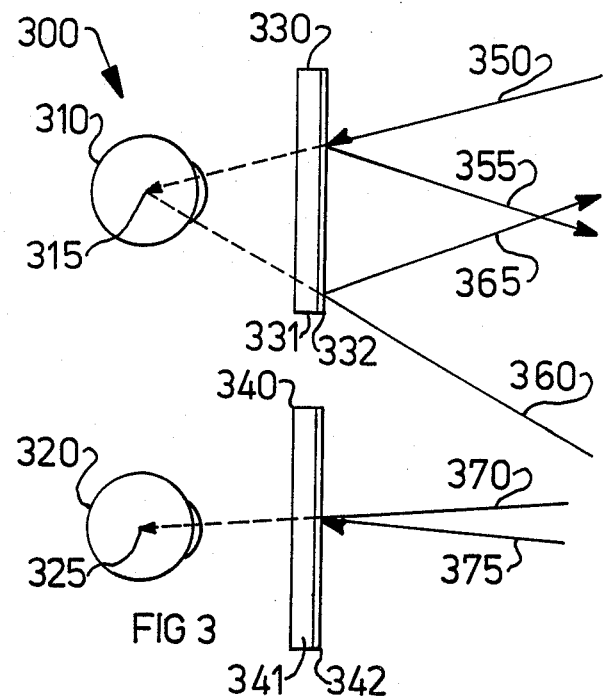
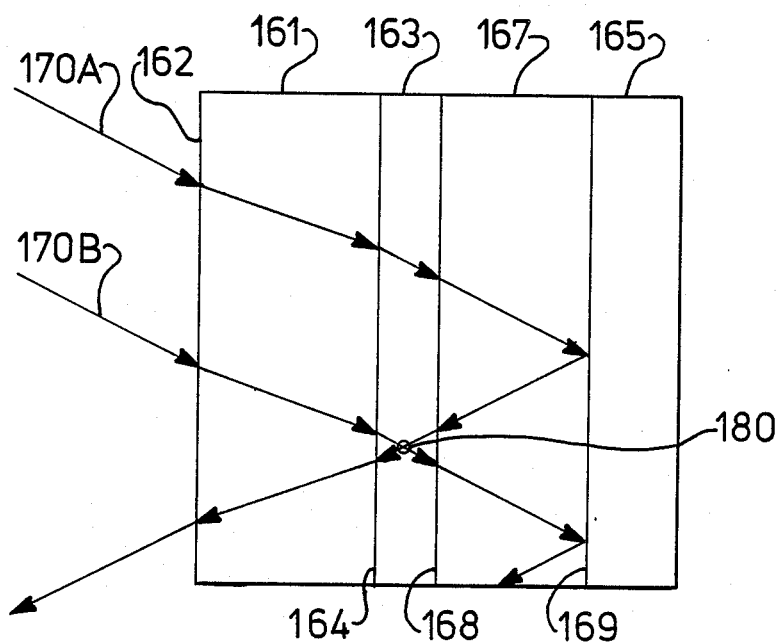
FIG 3
FIG 4

HOLOGRAPHIC FILTER CONSTRUCTION FOR PROTECTIVE EYEWEAR1

FIELD OF THE INVENTION

The field of the present invention is protection of a user's eye from laser radiation.

BACKGROUND OF THE INVENTION

Due to recent advances in the technology of laser generation and detection, laser systems for use in battlefield conditions have become more and more prevalent. These laser systems are employed for target illumination and tracking or for ranging. In a particular battlefield setting, there may be numerous laser illuminators operating simultaneously. These laser illuminators may be both from friendly forces and from enemy forces. In particular, combat troops operating in this environment will be subject to uncontrolled illumination by laser radiation. Because of the great radiated power from these laser radiation sources, these personnel require some eye protection from this laser illumination. Heretofore, two differing types of laser eye protection have been proposed. The first type includes heavily tinted spectacles. The color of these tinted spectacles covers the bandwidth of the expected laser illumination. The laser light is absorbed by the tint in the spectacles, thereby reducing the light intensity reaching the user's eyes within the wavelength band of the tint.

The use of tinted spectacles has several problems. Firstly, it is difficult to obtain dyes having the necessary absorption band to cover the expected wavelengths of laser illumination. In addition, there is a disadvantageous tradeoff between the amount of protection provided and the reduction of visibility at other wavelengths. Because the absorption band of such tinted spectacles does not correspond to the rather narrow bandwidths of the laser illumination, such tinted spectacles necessarily absorb light at a far greater range of wavelengths than necessary to provide protection. In addition, in order to obtain the desired attenuation of the light at the particular laser illumination frequencies, it is necessary to heavily tint the spectacles. As a consequence, spectacles of this type which are tinted heavily enough in order to provide adequate protection also greatly reduce the visibility of the user at other wavelengths.

A second solution to this problem is the use of holographic optical elements. Holographic optical elements include three-dimensional interference fringe patterns which diffract light at specified wavelengths. Holographic optical elements are ordinarily constructed employing laser illumination forming interference fringes within the volume of a photosensitive medium. Upon development of the photosensitive medium, the pattern of the interference fringes is formed within this medium in the form of varying indexes of refraction. When light of certain wavelengths enters such a holographic optical element, it is diffracted by the interference pattern therein. In the case of laser protection eyewear, it is common to form a reflection holographic optical element which reflects incoming radiation at the particular wavelength in a manner making it appear to be a mirror.

Laser protective eyewear formed in this manner have heretofore been constructed employing spherical geometries concentric about an exposure point source used in construction of the holographic optical element. If the exposure point source is located at the position of the center of rotation of the eye, the geometry requires that the eyewear either have a shape concentric about the center of rotation of the eye or the interference fringes will intersect the surface of the eyewear. Because the construction of highly curved eyewear about the center of the eye is difficult, these holographic optical elements have generally been constructed with relatively flat surfaces. This causes the interference fringes, which are concentric with the center of rotation of the eye, to intersect the front and back surfaces of the spectacles at numerous places. This geometry can cause or aggravate a type of noise phenomenon called flare. This source of flare can be eliminated while still employing a relatively flat holographic optical element by locating the exposure point source at the center of curvature of the element, which would be further from the element than the center of rotation of the eye. This technique would provide interference fringes relatively parallel to the surface of the eyewear, thereby reducing the source of flare.

The use of such spherical geometries requires a disadvantageous compromise to provide the necessary angular protection for the user. Because the eye of the user can rotate, the laser protective eyewear must block radiation at a particular wavelength over a range of angles. At any particular rotated position of the eye harmful radiation can be received from a relatively narrow range of angles through only a small region of the eyewear. This narrow range of angles differs for different rotated positions of the eye, thus the total angular coverage needed is rather broad. Holographic optical elements constructed using spherical geometries are uniform relative to rotation of the eye. Thus the entire holographic optical element must block the particular wavelength throughout the broad range of angles. Known techniques for covering such broad angular ranges also broaden the band of wavelengths blocked. The broadened band of wavelengths reduces the transmissibility of the laser protective eyewear unnecessarily. In addition, the use of concentric geometry in the formation of such holographic optical elements, means that incoming radiation directed normal to the surface of the eyewear is retroreflected, that is reflected directly back toward the source. This causes the eye protection wearer to be a cooperative target to any enemy laser illuminations. Thus, a group of combat troops employing these laser protection spectacles would be readily visible in laser illumination from enemy troops.

SUMMARY OF THE INVENTION

It is an object of the present invention to provide a method of laser eye protection in a holographic optical element which reduces flare interference and does not provide a cooperative target to enemy laser illumination. This method involves the construction of a holographic optical element in which the interference geometry is conformal to the geometry of the holographic optical element. This technique provides interference fringes which are generally parallel to the surface of the holographic optical element but which have varying fringe spacings, thereby reducing the intersections of the interference fringes with the surface of the holographic optical element. This geometry allows for the use of flare prevention techniques such as disclosed in U.S. patent application Ser. No. 927,341, filed Nov. 4, 1986 entitled "Method for Forming Holographic Optical Elements Free of Secondary Fringes" which is a continuation of U.S. patent application Ser. No. 613,901, filed May 24, 1984, now abandoned. This construction technique results in a holographic optical element which is not uniform in relation to rotation of the eye of the user. Each small region of the eyewear may be constructed to block radiation at the particular wavelength arriving from only the relatively narrow range of angles which would reach the eye of the user through that small region. Thus each portion of the eyewear need block radiation arriving at a narrower range of angles than that according to the prior art. As a result the band of wavelengths blocked is narrower, increasing the transmissibility of the eyewear without sacrificing protection. In addition, the use of geometry other than spherical provides for reflection from the holographic optical element which is not retroreflective at all angles. That is, incoming laser illumination at many angles is not reflected back to the source but in another direction.

The holographic optical element constructed in the present invention is formed using a laser point source and a reflecting surface conformal to the surface of the photosensitive medium. The photosensitive medium is applied to the back surface of a transparent supporting substrate which becomes a part of the laser protection eyewear. A reflector is located in close proximity to the surface coated with a photosensitive medium, and it has a curvature that conforms to the curvature of the coated surface. This reflector can be directly applied to the outside surface of the photosensitive medium or may be a fixed surface which is optically coupled to the outside surface of the photosensitive medium via an index-matching fluid. An alternative technique employs the difference in index of refraction between the photosensitive medium and atmospheric air beyond the photosensitive medium. This difference in index of refraction causes partial reflection at the outer surface of the photosensitive medium. The holographic optical element is constructed employing a laser point source disposed at an exposure point with relation to the photosensitive medium which illuminates the photosensitive medium. Interference patterns are formed between the light arriving in the photosensitive medium directly from the laser point source and refelected light. After exposure, the photosensitive medium is developed to form the holographic optical element having interference fringes corresponding to the interference pattern formed by the direct and reflected beams during construction.

This holographic optical element is employed in protection of the eye of a user by disposing it before the eye with the center of the eye having the same relationship to the completed holographic optical element as the relationship the exposure point had to the photosensitive medium. In this event, if any laser light having the same wavelength as the laser point source used in construction crosses the holographic optical element on a path toward the center of the eye, this light is diffracted by the interference fringes in the holographic optical element. In addition, there are known techniques for forming a holographic optical element such that laser light having a differing wavelength from the wavelength of the laser point source used in construction is diffracted by the interference fringes on the holographic optical element. The result of this diffraction is the same as if the incoming laser light encountered a reflector having the same surface as the surface of the mirror employed in construction. Light of other wavelengths incident upon the holographic optical element directed toward the center of the eye are relatively unchanged by the holographic optical element. Thus, this holographic optical element provides a notch filter for reflecting incoming laser radiation having a predetermined wavelength.

The present construction technique is advantageous for several reasons. Firstly, by the use of a reflecting surface conformal to the outer surface of the photosensitive layer, the interference fringes formed are inherently substantially parallel to the surface of the photosensitive layer. Thus, there are relatively few intersections between the interference fringes and the surface of the photosensitive layer. This geometry permits the use of flare reduction techniques as noted above. Because the resulting holographic optical element is not uniform with regard to rotation of the eye, the holographic optical element may be constructed with more limited angular coverage for each portion of the element. As noted above this increases the transmissibility of the eyewear without sacrificing protection. In addition, by adapting the reflector geometry conformal to the photosensitive layer, which is not concentric with the center of the eye, incoming laser radiation is not always retroreflected back to the source. This serves to prevent the wearer from becoming a cooperative target to enemy laser illumination.

BRIEF DESCRIPTION OF THE DRAWINGS

These aspects and the objects of the present invention will become clear from a study of the foregoing description and the figures in which:

FIG. 3 illustrates the use of a pair of holographic optical elements constructed in accordance with FIG. 1 in protection of two eyes of a user;

FIG. 4 illustrates the cross section of the holographic optical element during construction in accordance with a further embodiment of the present invention;

DETAILED DESCRIPTION OF THE PREFERRED EMBODIMENT

Figure 1:
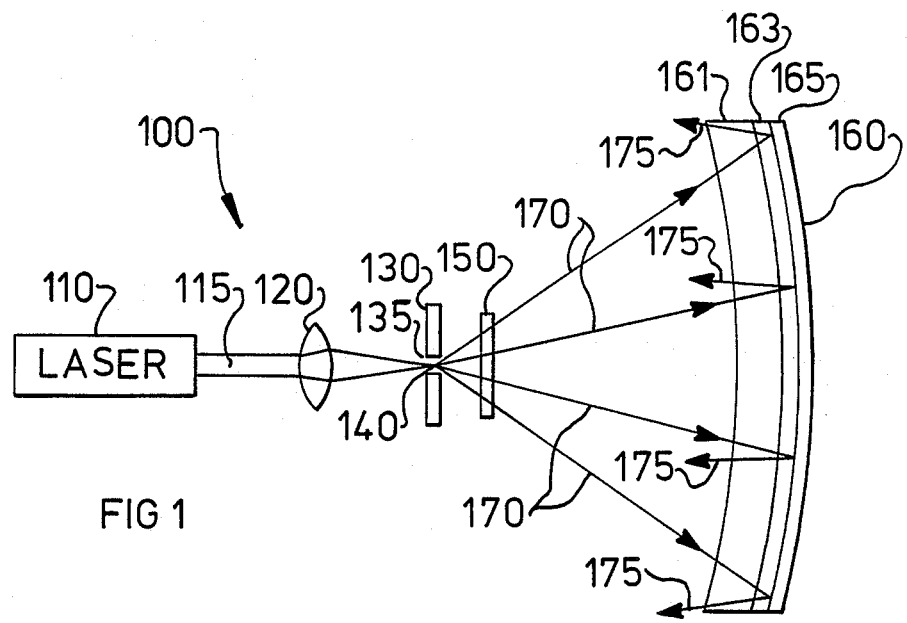
FIG. 1 illustrates the manner of construction of a holographic optical element in accordance with a first embodiment of the present invention.

FIG. 1 illustrates construction geometry 100 which is the preferred embodiment for construction of the holographic optical element in accordance with the present invention. FIG. 1 illustrates laser 110 which generates a beam of laser light 115. Laser 110 must generate laser beam 115 having a wavelength which is related to the wavelength at which the holographic optical element will provide protection to the user. In the preferred embodiment, the wavelength of the laser light beam 115 from laser 110 is different than wavelength of the laser light at which the eyewear will provide protection. In the preferred embodiment illustrated in FIGS. 1 to 5, this laser protective eyewear is a set of spectacles.

Laser light beam 115 is applied to condensing lens 120 which focuses this beam of light upon pinhole 135 in mask 130. This produces the effect of a laser point source at point 140 in the center of the pinhole 135. The term point source as used herein can refer to the area of minimum cross section of an aberrated construction beam.

Light rays 170 emanating from point source 140 pass through a moving diffuser 150. The purpose of moving diffuser 150 is to reduce the coherence length of the light rays 170, in a manner that will be more fully explained below. Light rays 170 are applied to spectacle lens 160 which includes a transparent supporting substrate 161, a photosensitive layer 163 and a reflecting layer 165. Transparent supporting substrate 161 could be constructed of glass or plastic, for example. The light passes through transparent supporting substrate 161 and through the photosensitive layer 163, which is partially transparent. This light is reflected from reflecting layer 165 and becomes return rays 175. Note that the return rays 175 follow different paths than the original light rays 170. The original and return paths would be coincident only if spectacle lens 160 was a portion of a sphere and the exposure point 140 was at the center of curvature of this spherical shape. In general, the construction geometry illustrated at 100 in FIG. 1 requires that the exposure point 140 be closer to the spectacle lens 160 than the center of curvature of the reflecting layer 165.

Figure 2:
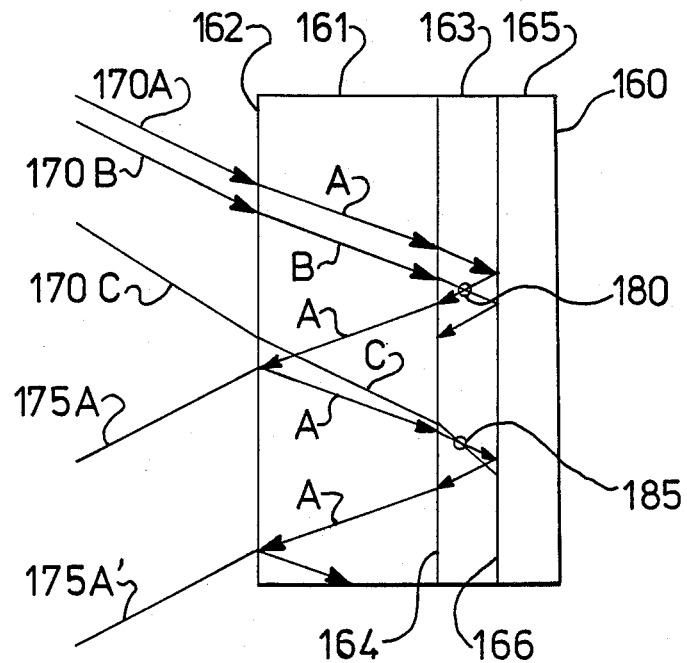
FIG. 2 illustrates a detailed cross section of the holographic optical element during construction as illustrated in FIG. 1.

FIG. 2 illustrates a detail of the cross section of spectacle lens 160 during construction. A light ray 170A incident upon transparent supporting substrate 161 is refracted at the air/substrate interface 162. This beam then passes through transparent supporting substrate 161 and hence to photosensitive layer 163. Again, this light ray 170A may be slightly refracted at the interface 164 between the transparent supporting substrate 161 and the photosensitive layer 163. The light passes through photosensitive layer 163 reaching reflective surface 166 of reflecting layer 165. The light is reflected at reflecting surface 166 of reflecting layer 165 and passes back through photosensitive layer 163. A companion light ray 170B also passes through the air/substrate interface 162, transparent supporting substrate 161, the interface 164 and hence into photosensitive layer 163. These two light rays cross and interfere at area of interference 180. This interference between the two light rays, one coming directly from point source 140 and one reflected from reflecting layer 165, changes the properties of photosensitive layer 163.

Light ray 170A continues through the interface 164 and the transparent supporting substrate 161 out of the spectacle lens 160 and becomes reflected ray 175A. Because of the difference in indexes of refraction between the air on one side of interface 162 and the transparent supporting substrate 161 on the other side, some of this light is reflected back into transparent supporting substrate 161 at interface 162. This further reflected ray passes back through transparent supporting substrate 161 and into photosensitive layer 163. This further reflected ray may interfere at position 185 with a direct light ray 170C arriving at a slightly different angle. This interference at point 185 between the direct light from point source 140 and an internally reflected ray is an undesired interference which forms a secondary interference pattern or secondary hologram. Such secondary interference patterns will tend to cause ghosts in the image seen through the holographic optical element and hence are undesirable. Moving diffuser plate 150 is employed to reduce or eliminate the formation of such secondary interference patterns.

Moving diffuser 150 serves to reduce the coherence length of the light emitting from point source 140. Typically the output of laser 110 is highly coherent, that is it has a long coherence length relative to the dimensions of the structures of FIG. 2. Coherence length is defined as the maximum path length difference between two light beams derived from the primary light beam which enables the formation of interference fringes. Ordinarily, laser light beam 115 from laser 110 has a relatively long coherence length, that is interference fringes can be formed having a large path length difference. In such a case, the path directly from point source 140 to photosensitive layer 160, such as light ray 170C, has a path length difference from the path length of light ray 170A, which is reflected from the interface 162 from transparent supporting substrate 161, such that interference fringes are formed. In addition, interference fringes can also be formed from further reflections of either or both of these light beams from point source 140. Thus, a point source 140 formed of light having a long coherence length permits the formation of numerous secondary holograms.

Reduction of the coherence length of the light from point source 140 is advantageous in reducing the incidence of these secondary holograms. Firstly, the moving diffuser 150 reduces the coherence length to a length which is still greater than the path length difference of direct light from point source 140 and light from point source 140 reflected from reflection surface 166 of reflecting layer 165. Thus interference fringes continue to be formed in the area 180 as illustrated in FIG. 2. However, the reduced coherence length of the point source 140 is less than the path length difference from a light ray reaching photosensitive layer 163 directly and a light ray which is reflected from reflection surface 166, further reflected from interface 162 and transmitted to photosensitive layer 163. This reduction in coherence length ensures that interference fringes are not formed by the light paths that intersect at the area 185 as illustrated in FIG. 2. Thus the use of moving diffuser 150 reduces the formation of secondary fringes.

Construction of the spectacle lens 160 continues with the development of photosensitive layer 163. Firstly, the reflecting layer 165 is removed from the outer surface of photosensitive layer 163. If reflecting layer 165 is a vapor deposited metal layer, then this removal may be achieved by an acid bath. Since only a very thin reflecting layer is required to construct the holographic optical element, removal in this manner would not take a great deal of time. In the preferred embodiment, photosensitive layer 163 is a dichromated gelatin, although other photosensitive materials could be used. After exposure this layer is developed by known methods. The result is a layer which has a predetermined thickness, is generally very transparent and has a modulated index of refraction throughout its volume dependent upon the exposure. This modulation in the index of refraction is what causes the layer to diffract light.

In some applications, the holographic optical element is exposed at a wavelength that is different from the use wavelength, or the wavelength that is to be rejected by the protective eyewear. This may happen, for example, when the recording material is not photosensitive at the use wavelength, or when lasers suitable for recording holograms are not available at the use wavelength. When a wavelength shift is encountered, compensation must be provided to account for the change in wavelength between construction and use. Compensation for the wavelength shift may be accomplished by two methods known in the art which may be used singly or in combination. First, the location of the exposure point sources may be altered to compensate for the effects of changing the wavelength. The exposure points are relocated to create an interference pattern at the construction wavelength that has the parameters required by the holographic optical element at the use wavelength. Secondly, the holographic recording material may be altered in processing to compensate for the wavelength shift. For example, if the spacing between interference fringes is increased by swelling the material, the use wavelength of the element will increase relative to the construction wavelength. Alternatively, if the spacing between the interference fringes is decreased by shrinking the material, the use wavelength will decrease relative to the construction wavelength. Only if the photosensitive layer is neither swelled nor shrunk during development and the holographic optical element is used with the eye located at the exposure point, will the use wavelength equal the construction wavelength.

FIG. 3 illustrates an example of the use of the holographic optical elements thus formed in protection of the eyes. FIG. 3 illustrates left eye 310 having a center 315 and right eye 320 having a center 325. Spectacle lens 330 including transparent supporting substrate 331 and holographic optical element 332 is disposed in front of the left eye 310. Similarly, spectacle lens 340 which includes transparent supporting substrate 341 and holographic optical element 342 is disposed in front of the right eye 320. The center 315 of the left eye 310 and the center 325 of right eye 320 are located relative to the respective spectacle lenses 330 and 340 in a manner having a predetermined relationship to the position of the exposure point during exposure to provide protection of the eyes at the user wavelength.

The interference fringes within holographic optical elements 332 and 342 serve to reflect incoming light having a predetermined wavelength related to the spacing of interference fringes. For example, incoming laser ray 350 is directed toward center 315 of left eye 310. Instead of continuing through the spectacle lens 330 to the center of the eye, this light is diffracted by the interference fringes within holographic optical element 332. This diffraction makes the spectacle 330 act like a mirror within a range of wavelengths near the threatening wavelength. Thus incoming laser light 350 is reflected away as ray 355. Similarly, incoming laser ray 360 directed toward center 315 of left eye 310 is effectively reflected as illustrated by ray 365. In a like manner, incoming ray 370 directed toward the center 325 of the right eye 320 is effectively reflected by the holographic optical element 342 and becomes ray 375.

The method of construction illustrated in FIG. 1 is highly advantageous for constructing the spectacles illustrated in FIG. 3. The use of laser beam 115 from laser 110 having a particular selected frequency automatically causes the interference pattern within holographic optical elements 332 and 342 to have the fringe spacings required for diffraction of light having a predetermined wavelength. In general, the effective shape of the mirror formed by the holographic optical element is independent of the actual geometry of the holographic optical element. The geometry of the effective mirror formed by the holographic optical element is determined by the geometry of the interfering light employed to form these elements. Thus employing the geometry illustrated in FIG. 1 causes the effective mirror formed by holographic optical elements 332 and 342 to be conformal to the surface of these holographic optical elements. This is because the second light beam employed to form the holographic optical element from photosensitive layer 163 is generated by the reflective layer 165 which is conformal to the surface of the photosensitive layer 163.

Holographic optical elements intended for use as laser eye protectors have heretofore been constructed employing spherical geometries. Examples of such construction is shown in U.S. Pat. No. 4,601,533 entitled "Laser Eye Protection Visor Using Multiple Holograms" issued to Moss on July 22, 1986 and Patent Cooperation Treaty Published Application No. WO83/04317 entitled "Holographic Laser Protection Device" published on Dec. 8, 1983, now U.S. Pat. No. 4,637,678. In accordance with the prior technique disclosed in these two references, the holographic optical element was constructed employing a geometry concentric about the center of the eye.

This construction technique leads to a disadvantageous trade off between ease of construction and flare. Flare is the undesirable diffraction of light caused by spurious secondary holograms and by tilt of the holographic fringes. When the holographic optical element for eye protection is constructed employing a spherical geometry, the interference fringes are inherently spherical and concentric about the location of the exposure point employed in its construction. In this case, flare caused by the fringe tilt can be minimized by constructing the spectacle lens in an approximation of the spherical shape of the interference fringes. However, construction of such a shape concentric with the center of the eye is unduly restrictive. If a flatter curvature is employed for the holographic optical element, then the holographic fringes will be tilted relative to the surface of the holographic optical element, and may contribute to flare. Thus, in accordance with the construction technique of the prior art, there is a disadvantageous trade off between the reduction of flare and the amount of design flexibility of the spectacle lens.

Construction of laser protection eyewear having holographic optical elements with effective spherical geometries involves further disadvantages. The angular coverage required over the whole holographic optical element is greater than necessary thus reducing the transmissibility of the eyewear. Light of the selected wavelength when directed toward the center of the eye is reflected directly back toward the source. In an environment in which enemy forces are employing laser trackers or laser target designators, the retroreflection of the laser light from laser protection spectacles means that personnel using these laser protection spectacles are cooperative targets. This is a clear disadvantage when operating in a hostile combat environment.

Figure 5:
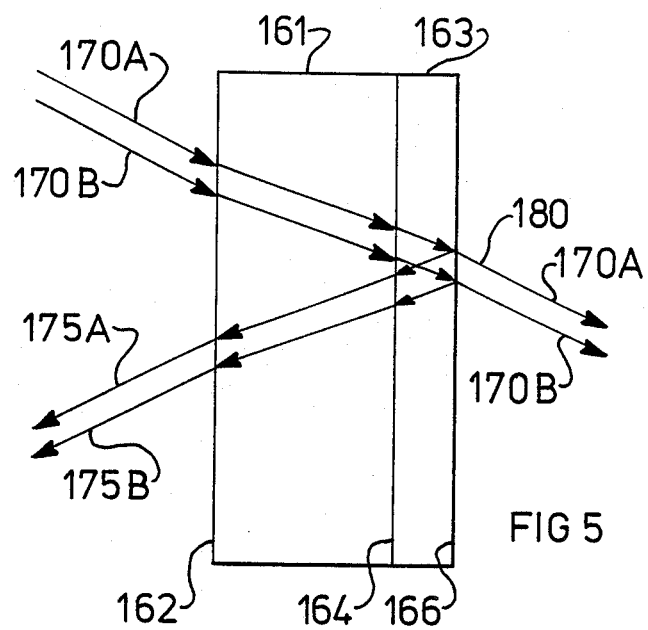
FIG. 5 illustrates the cross section of the holographic optical element in accordance with a still further embodiment for construction of the present invention.

FIGS. 4 and 5 are analagous to FIG. 2. These figures illustrate alternative techniques for forming the reflecting surface employed in the construction geometry 100 illustrated in FIG. 1.

FIG. 4 illustrates a second embodiment for providing the reflecting surface required for the formation of the holographic optical element in accordance with the present invention. FIG. 4 is a cross section of a small portion of the supporting substrate, photosensitive layer and mirror which can be employed in the construction geometry illustrated in FIG. 1. In FIG. 4, a fixed mirror 165 having a reflective surface 169 is employed. Reflecting surface 169 must be conformal to the outer surface of photosensitive layer 168. However, it is contemplated that a relatively permanent fixed mirror will be employed in this embodiment.

Transparent supporting substrate 161 together with the photosensitive layer 163 formed on one surface thereof is disposed in proximity to the mirror 165. The gap between the external surface 168 of photosensitive layer 163 and the reflecting surface 169 of mirror 165 is filled with an index matching fluid 167. This index matching fluid 167 is selected to have an index of refraction which is substantially equal to the index of refraction of photosensitive layer 163.

Light ray 170A coming from point source 140 crosses transparent supporting substrate 161, photosensitive layer 163, index matching fluid 167 and is reflected from the reflecting surface 169. In this regard note that the light ray is refracted at interface 162 between the air and the transparent supporting substrate 161, but is only slightly refracted at interface 164 between transparent supporting substrate 161 and photosensitive layer 163, and at interface 168 between photosensitive layer 163 and index matching fluid 167. There is little or no refraction at the boundaries 164 and 168 because the indexes of refraction across these boundaries are substantially the same. A second light ray 170B crosses transparent supporting substrate 161 and enters the photosensitive layer 163. These two light rays interfere in an area 180. This interference is the same as previously illustrated in FIG. 2, with the exception that the reflecting surface 169 is somewhat further away from the photosensitive layer 163 than illustrated in FIG. 2.

This technique has the advantage of not requiring the formation of a reflecting layer 165 on the surface of photosensitive layer 163 and then later removing this reflecting layer. On the contrary, the embodiment illustrated in FIG. 4 employs a relatively permanent mirror 165 which can be employed in the construction of a plurality of holographic optical elements.

FIG. 5 illustrates a further embodiment for construction of the holographic optical element according to the geometry illustrated in FIG. 1. In FIG. 5, there is no structure placed on the external surface of photosensitive layer 163. Rather, the normal atmospheric air is beyond the surface 166 of photosensitive layer 163. A ray of light 170A passes through transparent supporting substrate 161 and photosensitive layer 163, and is partly reflected at the outer surface 166 of photosensitive layer 163. This partial reflection causes interference between the reflection of ray 170A and ray 170B at interference region 180.

The construction technique illustrated in FIG. 5 is advantageous because it does not require any additional elements beyond the transparent supporting substrate and the photosensitive layer. However, because the internal reflections are less intense than in the case using a reflecting layer 165, a longer exposure time would be required in order to form the holographic optical element in accordance with this embodiment.

Figure 6:
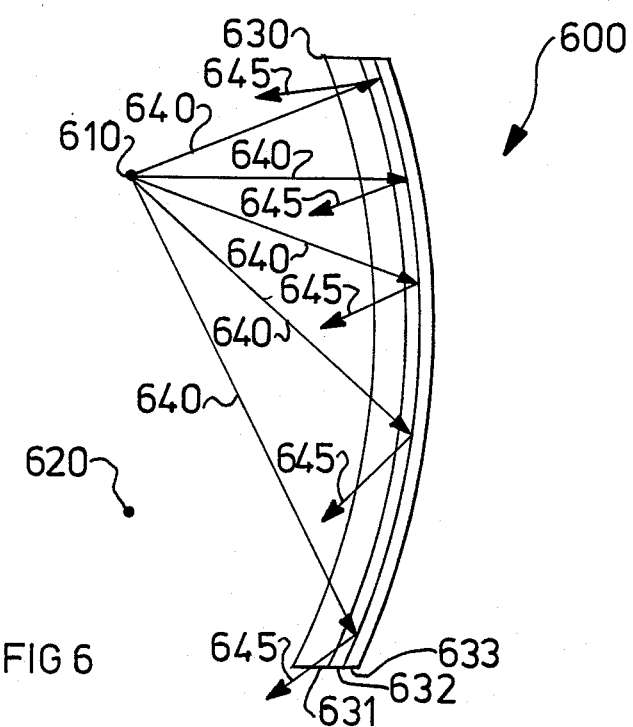
FIG. 6 illustrates the first step in construction of a visor for protection of both eyes.
Figure 7:
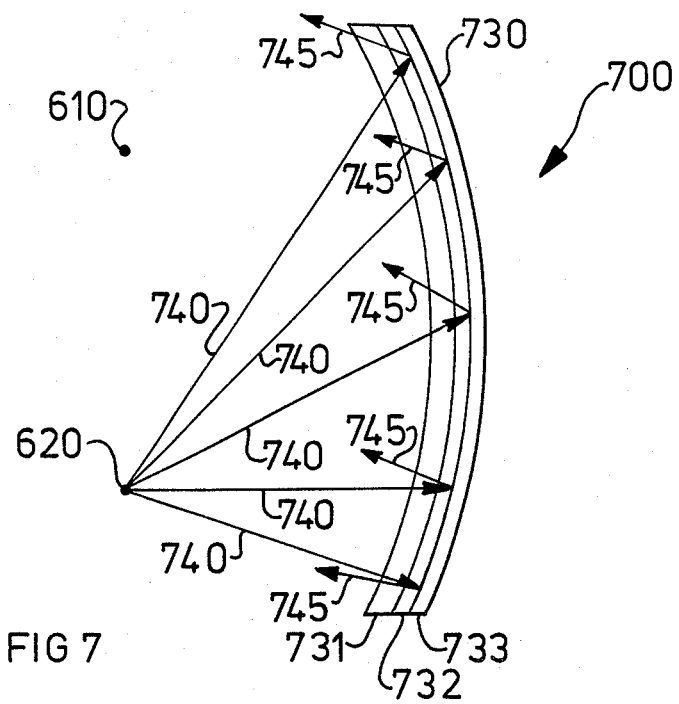
FIG. 7 illustrates the second step in construction of a visor for protection of both eyes.
Figure 8:
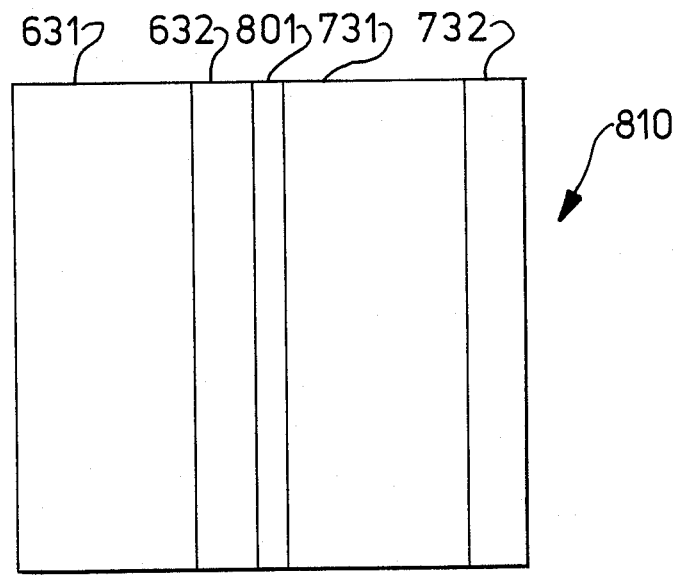
FIG. 8 illustrates the details of the cross section of the assembled visor in accordance with the present invention.
Figure 9:
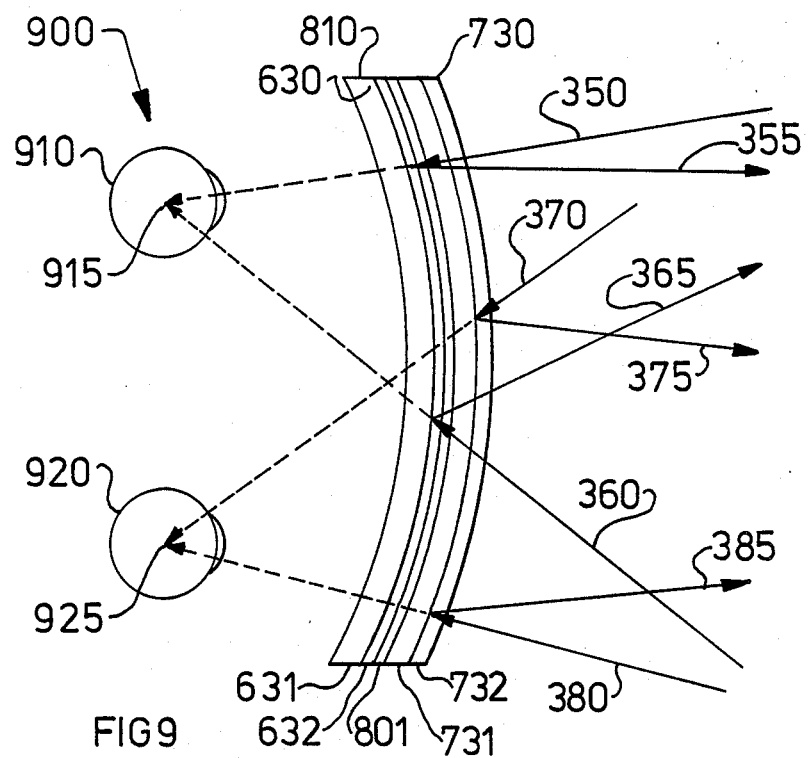
FIG. 9 illustrates the use of the visor constructed in accordance with FIGS. 6 and 7 in protection of both eyes of the user.

FIGS. 6 to 9 illustrate the construction and use of a visor for protecting both eyes of the user. FIGS. 6 and 7 illustrate the manner of construction of two portions of the visor, FIG. 8 illustrates a cross section of the completed visor and FIG. 9 illustrates the visor in use.

FIG. 6 illustrates the first step in construction of a visor for protection of both eyes. FIG. 6 illustrates construction geometry 600 including point source 610 corresponding to the location of the center of the left eye and point 620 corresponding to the center of right eye. Visor element 630 includes transparent supporting substrate 631, photosensitive layer 632 and reflecting layer 633. An exposure point source such as illustrated in FIG. 1 is disposed at point 610 and is allowed to expose the photosensitive layer 632. For the sake of simplicity, this is shown schematically. Also note that this construction may also employ a diffuser such as diffuser 150 to prevent the formation of secondary holograms. A plurality of rays 640 are directed to the visor element 630 and reflected rays 645 emanate from the reflecting layer 633. FIG. 6 illustrates the construction geometry illustrated in detail in FIG. 2. It would be understood by those skilled in the art that construction geometry 600 illustrated in FIG. 6 could also be embodied employing the alternative techniques illustrated previously in FIGS. 4 and 5.

After exposing photosensitive layer 632, this photosensitive layer is developed. This is achieved by removing the reflecting layer 633 and then developing the photosensitive layer 632. The resulting visor element 630 forms a portion of the visor to be constructed.

FIG. 7 illustrates the next step in construction of the laser eye protection visor. FIG. 7 illustrates a exposure point source disposed at point 620 corresponding to the center of the right eye. Also note point 610 corresponding to the center of the left eye. Visor element 730 is disposed at a position in proximity to the relative position of visor element 630 illustrated in the construction geometry shown in FIG. 6. In the construction geometry 700 the inner surface of transparent supporting substrate 731 is conformal to the position of the outer surface of photosensitive layer 632 in the construction geometry 600. Visor element 730 includes transparent supporting substrate 731, photosensitive layer 732 and reflecting layer 733. As illustrated in FIG. 7, light rays 740 from a laser point source 620 are allowed to illuminate the visor element 730. Light rays 740 directly expose photosensitive layer 732. Photosensitive layer 732 is also exposed by reflecting rays 745 reflected from the inner surface of reflecting layer 733. In accordance with the principles previously described, this causes a change in the photosensitive layer 732 to form interference fringes therein.

FIG. 8 illustrates a cross section of the completed visor. The reflecting layer 733 is removed from visor element 730 leaving only transparent supporting substrate 731 and photosensitive layer 732. Visor element 730 is combined with visor element 630 to form the visor cross section 810 illustrated in FIG. 8. This includes transparent supporting substrate 631, holographic optical element layer 632, transparent adhesive layer 801, transparent supporting substrate 731 and holographic optical element layer 732. Transparent adhesive layer 801 is disposed between the photosensitive layer 632 and the transparent supporting substrate 731 in order to bond the two portions of the visor together. Together the two holographic optical element layers 632 and 732 will cooperate to protect both eyes. A protective layer or cover plate may be subsequently added to protect optical element layer 732.

FIG. 9 illustrates the operation of a visor 810 in protection of left eye 910 and right eye 920. Left eye 910 has center 915 located at the position 610 relative to visor element 630 which is a part of visor 810. Similarly, right eye 920 has a center 925 located at position 620 in relationship to the visor element 730 which is a part of visor 810.

In use, light directed toward the center of either eye is diffracted and effectively reflected away from the eye. Incoming ray 350 is directed toward center 915 of left eye 910. This incoming ray is diffracted by holographic optical element layer 632 and effectively reflected away along ray 355. Similarly, ray 360 directed toward center 915 of left eye 910 is diffracted by holographic optical element layer 632 and effectively reflected as ray 365. In a similar manner, ray 370 directed toward the center 925 of right eye 920 is diffracted by holographic optical element layer 732. This ray is effectively reflected away as ray 375. Ray 380 directed to the center 925 of right eye 920 is also effectively reflected from holographic optical element layer 732 and becomes reflected ray 385.

As indicated above, the effective shape of the reflector formed by the holographic optical element layers 632 and 732 is conformal to the geometry of these layers. Therefore, the incoming laser light is not always reflected directly back toward the source, but rather is reflected in differing directions. This serves to reduce the visibility of the visor 810.

Figure 10:
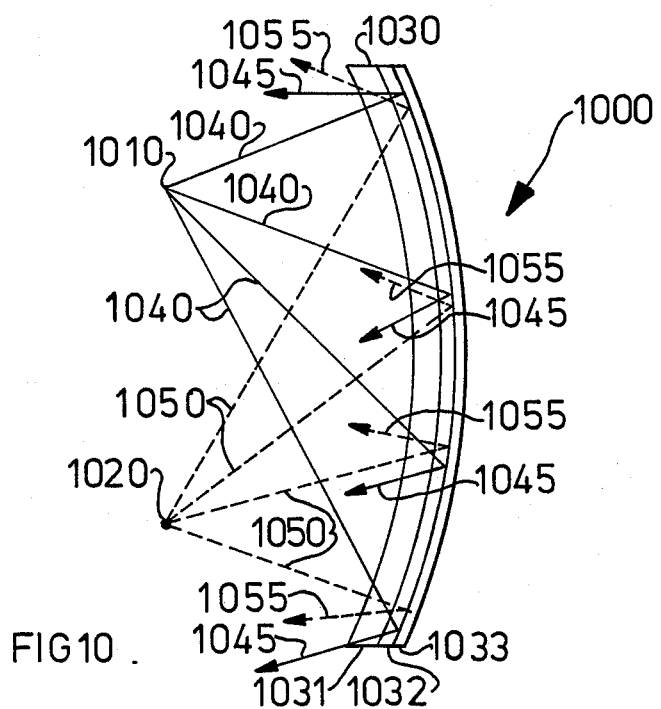
FIG. 10 illustrates an alternative manner of construction of a visor for protection of both eyes.

FIG. 10 illustrates construction geometry 1000 which is an alternative embodiment for construction of a visor to protect both eyes. FIG. 10 illustrates exposure points 1010 and 1020 which are used to expose a single photosensitive layer 1032. Photosensitive layer 1032 is disposed on transparent supporting substrate 1031 and has reflecting layer 1033 disposed on the outer surface thereof. Together these parts form visor element 1030.

Photosensitive layer 1032 is exposed by an exposure point source disposed at exposure point 1010 and by an exposure point source disposed at exposure point 1020. A first exposure point source at exposure point 1010 generates direct rays 1040 and reflected rays 1045 which are reflected from reflecting layer 1033. Similarly a second exposure point source at exposure point 1020 generates direct rays 1050 (shown in dashed lines) and reflected rays 1055 (also shown in dashed lines). The single photosensitive layer 1032 thus records interference fringes from both exposure sources. This visor may be used in the same manner as illustrated in FIG. 9.

The construction geometry 1000 can be formed in several ways. Firstly, photosensitive layer 1032 may be simultaneously exposed to two exposure point sources at exposure points 1010 and 1020. Alternatively, photosensitive layer 1032 may be exposed to exposure point sources at exposure points 1010 and 1020 sequentially. As an alternative to sequential exposure, a single exposure point source may be employed with visor element 1030 being shifted between exposures so that the two exposures occur from exposure points 1010 and 1020 relative to the visor element. Each of these alternatives results in the recording of two sets of interference fringes, one set of fringes for the protection of each eye. Although FIG. 10 illustrates visor element 1030 similar to spectacle lens 160 illustrated in FIG. 2, those skilled in the art would recognize that the construction techniques illustrated in FIGS. 4 and 5 could also be used.

Figure 11:
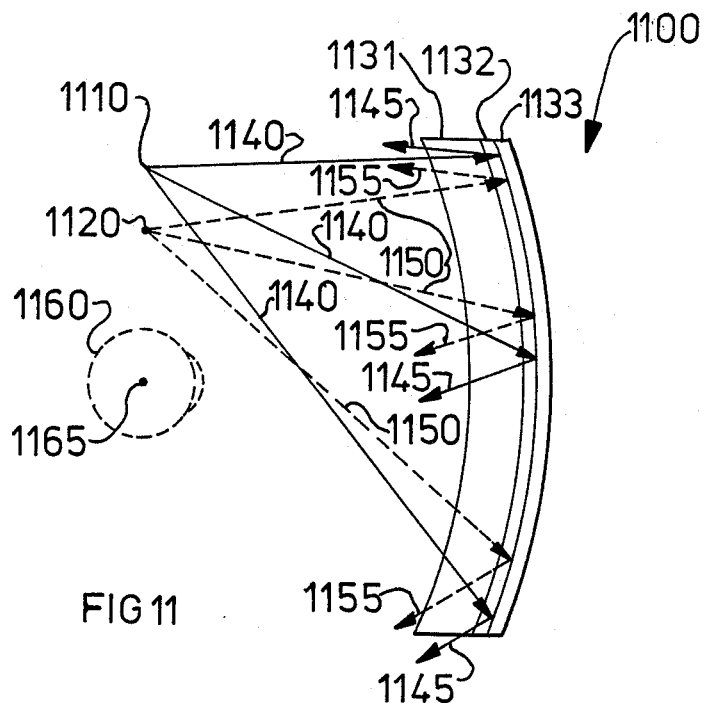
FIG. 11 illustrates a first embodiment for construction of eyewear for protection of the eye against plural laser radiation wavelengths.
Figure 12:
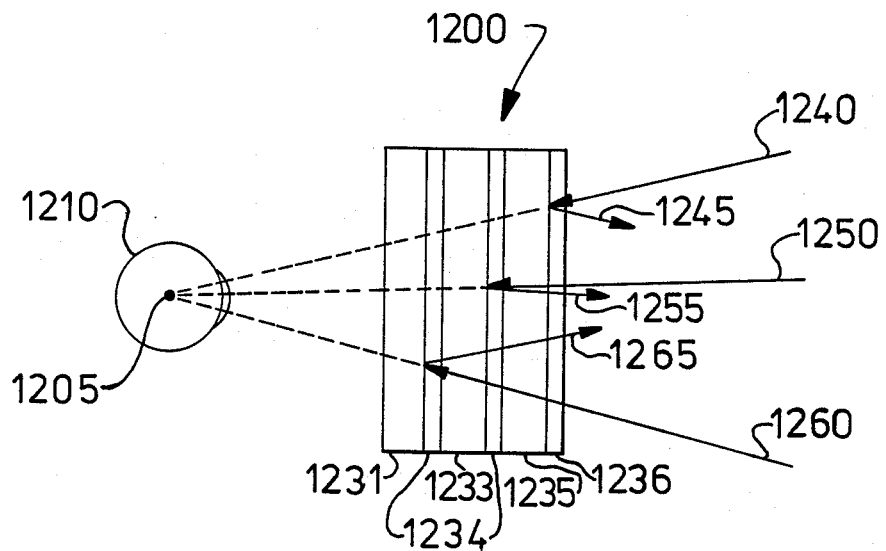
FIG. 12 illustrates an alternative embodiment for construction of eyewear for protection against plural laser radiation wavelengths.

FIGS. 11 and 12 illustrate alternative techniques for construction of laser protection eyewear which protects the eye against laser radiation occurring at plural wavelengths. FIG. 11 illustrates the construction of a single holographic optical element for protection against plural laser radiation wavelengths. FIG. 12 illustrates a construction employing plural holographic optical elements for protection of the eye against plural laser radiation wavelengths.

FIG. 11 illustrates construction geometry 1100 in which a single holographic optical element is constructed to protect against laser radiation at a plurality of wavelengths. Construction geometry 1100 illustrates a transparent supporting substrate 1131, a photosensitive layer 1132 and a reflecting layer 1133. These elements are assembled in accordance with the construction technique illustrated in FIG. 2. A pair of exposure points 1110 and 1120 are employed for exposing the photosensitive layer 1132. Rays 1140 from first exposure point 1110 are directed to photosensitive layer 1132 and reflecting layer 1133. An interference pattern is formed within photosensitive layer 1132 from the interference of rays 1140 and reflected rays 1145. Construction geometry 1100 illustrates a similar second exposure point 1120. Light rays 1150 from second exposure point 1120 are likewise directed toward photosensitive layer 1132 and reflecting layer 1133. Interference patterns are likewise formed between the rays 1150 and the reflected rays 1155 which are reflected from reflecting layer 1133.

Construction geometry 1100 also illustrates the proposed position of eye 1160 with its center 1165. Note that both the first exposure point 1110 and the second exposure point 1120 are displaced from the center 1165 of eye 1160. Also note that two sets of interference patterns are formed from the light coming from the two exposure points. These two sets of interference patterns coexist in the same manner as the two sets of interference patterns illustrated in FIG. 10. Because of the differing displacement from the center 1165 of eye 1160 of the first exposure point 1110 and the second exposure point 1120, the interference patterns formed within photosensitive layer 1132 have differing fringe spacings. Upon development of photosenstive layer 1132, these two sets of interference patterns with the differing fringe spacings enable diffraction and effective reflection away from the eye 1160 of laser radiation directed toward the center 1165 of eye 1160 on two predetermined wavelengths. These two wavelengths are controlled by the exact placement of the first and second exposure points and the particular wavelength of the laser source employed in construction. Thus construction geometry 1100 enables construction of laser protection eyewear which protects the eye against laser radiation at two differing wavelengths.

Although construction geometry 1100 illustrated in FIG. 11 is shown in accordance with the construction geometry previously illustrated in FIG. 2, those skilled in the art would clearly understand that the construction technique illustrated in FIG. 4 or FIG. 5 could equally well be employed in construction geometry 1100. In addition, those skilled in the art would also understand that it is possible to employ more than two exposure points, thereby causing additional sets of interference patterns which would provide protection against additional laser wavelengths. This process cannot be continued without limit, however. In particular, with the use of a large number of exposure points, the photosensitive layer 1132 would be saturated, and incapable of providing distinguishing fringes which are necessary for diffraction of the laser radiation.

FIG. 12 illustrates a second embodiment of a technique for providing laser eye protection at a plurality of wavelengths. Use geometry 1200 illustrates eye 1210 having center 1205 and a plurality of tandem layers for laser eye protection. These layers include first transparent supporting substrate 1231, first holographic optical element layer 1232, second transparent supporting substrate 1233, second holographic optical element layer 1234, third transparent supporting substrate 1235 and third holographic optical element layer 1236. Each pair of corresponding transparent supporting substrate and holographic optical element layer may be constructed in accordance with the techniques illustrated in FIGS. 2, 4 or 5. In the geometry 1200 illustrated in FIG. 12, the interference pattern within the three holographic optical element layers are constructed for protection against differing predetermined threatening wavelengths. As illustrated in FIG. 12, incoming ray 1240 at the first predetermined wavelength directed toward a center 1205 of eye 1210 is diffracted and effectively reflected by third photosensitive layer 1236 and becomes reflected ray 1245. Similarly, ray 1250 directed toward the center 1205 of eye 1210 at the second predetermined wavelength is diffracted and effectively reflected by second holographic optical element layer 1234 and becomes reflected ray 1255. Lastly, incoming ray 1260 at the third predetermined wavelength directed toward center 1205 of eye 1210 is diffracted and reflected by first holographic optical element layer 1232 and becomes reflected ray 1265.

FIG. 12 thus illustrates the means by which the eye may be protected against a plurality of threatening laser wavelengths. Those skilled in the art would clearly understand that a differing plurality of pairs of transparent supporting substrate and holographic optical element layers may be employed other than the three pairs illustrated in FIG. 12. The number of such layers which may be employed is subject only to the limitation of the reduction in total light transmission of the structure when a large number of such pairs is employed.

I claim:
1. A method of providing laser eye protection comprising the steps of:
 (a) forming a photosensitive layer on the outer surface of a curved transparent supporting substrate having an approximate center of curvature;
 (b) disposing a reflecting surface conformal to the outer surface of said photosensitive layer for reflecting light inward from said curved transparent supporting substrate , said reflecting surface thereby having an approximate center of curvature;
 (c) exposing said photosensitive layer with a laser source having an area of minimum cross section located at an exposure point, said exposure point located a distance closer to said reflecting surface than said approximate center of curvature of said reflecting surface, thereby causing interference fringes in said photosensitive layer from the interference of light reaching said photosensitive layer directly from said laser source and light reflected from said reflecting surface;
 (d) removing said reflecting surface from said photosensitive layer; and
 (e) developing said exposed photosensitive layer to form a holographic optical element including said interference fringes;
 (f) disposing said holographic optical element before an eye of a user whereby the center of the eye is located at a position relative to said holographic optical element having a predetermined relationship to the position of said exposure point relative to said photosensitive layer during exposure of said photosensitive layer for wavelength shift whereby laser radiation having a predetermined wavelength related to the wavelength of said laser source directed toward the center of the eye is diffracted away from the eye in a direction that is not retroreflective for all angles of incidence.

2. The method of providing laser eye protection claimed in claim 1, wherein:
 said step of exposing said photosensitive layer (step(c)) includes the steps of
 (i) forming a light beam having a long coherence length relative to the thickness of the photosensitive layer; and
 (ii) limiting the coherence length of said light beam to a length adequate for forming interference fringes within the photosensitive layer without forming any secondary interference fringes that would result from the interference of light beams reflected from the inner surface of the supporting substrate with light beams traveling directly to the photosensitive layer from said laser source.

3. The method of providing laser eye protection claimed in claim 1, wherein:
 said step of disposing a reflecting surface conformal to the outer surface of said photosensitive layer (step(b)) comprises forming a layer of reflective material on the outer surface of said photosensitive layer; and
 said step of removing said reflecting surface from said photosensitive layer (step(d)) comprises removing said layer of reflective material from the outer surface of said photosensitive layer.

4. The method of providing laser eye protection claimed in claim 3, wherein:
 said step of forming a layer of reflective material on the outer surface of said photosensitive layer (step(b)) comprises vapor deposition of a reflecting material.

5. The method of providing laser eye protection claimed in claim 1, wherein:
 said step of disposing a reflecting surface conformal to the outer surface of said photosensitive layer (step(b)) comprises
 (i) constructing a reflecting surface conformal to the outer surface of said phtoosensitive layer,
 (ii) disposing said transparent supporting substrate in proximity to said reflecting surface whereby the outer surface of said photosensitive layer is adjacent to said reflecting surface with a gap therebetween, and (iii) filling said gap between the outer surface of said photosensitive layer and said reflecting surface with an index matching fluid having approxiamtely the same index of refraction as the index of refraction of said photosensitive layer;

said step of removing said reflecting surface from said photosensitive layer (step(d)) comprises (i) removing said index matching fluid from said gap between the outer surface of said photosensitive layer and said reflecting surface, and (ii) removing said transparent supporting substrate from proximity to said reflecting surface.

6. The method of providing laser eye protection claimed in claim 1, wherein:

said step of disposing said holographic optical element before the eye of a user (step(f)) by locating the center of the eye at a position relative to said holographic optical element differing from the position of said exposure point relative to said photosensitive layer during exposure of said photosensitive layer in a manner dependent upon the relationship between said predetermined wavelength and the wavelength of said laser source.

7. The method of providing laser eye protection claimed in claim 1, wherein:

said step of developing said exposed photosensitive layer (step(e)) includes changing the thickness of said photosensitive layer thereby changing the spacing of said interference fringes, whereby said predetermined wavelength differs from the wavelength of said laser point source by a factor dependent upon the ratio of the change in thickness of said photosensitive layer during development.

8. The method of providing laser eye protection claimed in claim 1, wherein:

said step of developing said photosensitive layer (step(e)) preserves the thickness of said photosensitive layer;

said step of disposing said holographic optical element before the eye of a user (step(f)) by locating the center of the eye at a position relative to the holographic optical element substantially the same as the position of said exposure point relative to the photosensitive layer during exposure of said photosensitive layer, whereby said predetermined wavelength is equal to the wavelength of said laser source.

9. The method of providing laser eye protection claimed in claim 1, wherein:

said photosensitive layer consists of dichromated gelatin.

10. A method of providing laser eye protection comprising the steps of:

(a) forming a photosensitive layer on the outer surface of each of two curved transparent supporting substrates, each curved transparent supporting substrate having a corresponding approximate center of curvature;

(b) disposing a reflecting surface conformal to the outer surface of said photosensitive layer of each curved transparent supporting substrate for reflecting light inward from each of said curved transparent supporting substrate each reflecting surface thereby having a corresponding approximate center of curvature;

(c) exposing each of said photosensitive layers with a laser source having an area of minimum cross section located at a corresponding exposure point, each exposure point located a distance closer to said corresponding reflecting surface than said corresponding approximate center of curvature of said reflecting surface, thereby causing interference fringes in said photosensitive layer from the interference of light reaching said photosensitive layer directly from said laser source and light reflected from said corresponding reflecting surface;

(d) removing said reflecting surface from each of said photosensitive layers; and (e) developing each of said exposed photosensitive layers to form a holographic optical element including said interference fringes;

(f) disposing one of said two holographic optical elements before each eye whereby the center of each eye is located at a position relative to the corresponding holographic optical element having a predetermined relationship to the position of said exposure point relative to the corresponding photosensitive layer during exposure of said photosensitive layer for wavelength shift, whereby laser radiation having a predetermined wavelength related to the wavelength of the corresponding laser source directed toward the center of either eye is diffracted away from the eye in a direction that is not retroreflective for all angles of incidence.

11. The method of providing laser eye protection claimed in claim 10, wherein:

said step of exposing each of said photosensitive layers (step(c)) includes the steps of (i) forming a light beam having a long coherence length relative to the thickness of the corresponding photosensitive layer; and (ii) limiting the coherence length of said light beam to a length adequate for forming interference fringes within the photosensitive layer without forming any secondary interference fringes that would result from the interference of light beams reflected from the inner surface of the supporting substrate with light beams traveling directly to the photosensitive layer from said laser source.

12. The method of providing laser eye protection claimed in claim 10, wherein:

said step of disposing said holographic optical element before the eye of a user (step(f)) by locating the center of the eye at a position relative to said holographic optical element differing from the position of said exposure point relative to said photosensitive layer during exposure of said photosensitive layer in a manner dependent upon the relationship between said predetermined wavelength and the wavelength of said laser source.

13. The method of providing laser eye protection claimed in claim 10, wherein:

said step of developing said exposed photosensitive layer (step(e)) includes changing the thickness of said photosensitive layer thereby changing the spacing of said interference fringes, whereby said predetermined wavelength differs from the wavelength of said laser point source by a factor dependent upon the ratio of the change in thickness of said photosensitive layer during development.

14. The method of providing laser eye protection claimed in claim 10, wherein:

said step of developing said photosensitive layer (step(e)) preserves the thickness of said photosensitive layer;

said step of disposing said holographic optical element before the eye of a user (step(f)) by locating the center of the eye at a position relative to the holographic optical element substantially the same as the position of said exposure point relative to the photosensitive layer during exposure of said photosensitive layer, whereby said predetermined wavelength is equal to the wavelength of said laser source.

15. The method of providing laser eye protection claimed in claim 10, wherein:
said photosensitive layer consists of dichromated gelatin.

16. A method of providing laser eye protection comprising the steps of:
(a) forming a photosensitive layer on the outer surface of a curved transparent supporting substrate, an outer surface of said photosensitive layer thereby having an approximate center of curvature;
(b) disposing atmospheric air beyond the outer surface of said photosensitive layer;
(c) exposing said photosensitive layer with a laser source having an area of minimum cross section located at an exposure point, said exposure point located a distance closer to said outer surface of said photosensitive layer than said approximate center of curvature, thereby causing interference fringes in said photosensitive layer from the interference of light reaching said photosensitive layer directly from said laser source and light reflected from the outer surface of said photosensitive layer due to the difference in index of refraction between said photosensitive layer and atmospheric air;
(d) developing said exposed photosensitive layer to form a holographic optical element including said interference fringes;
(e) disposing said holographic optical element before an eye of a user whereby the center of the eye is located at a position relative to said holographic optical element having a predetermined relationship to the position of said exposure point to said photosensitive layer during exposure of said photosensitive layer for wavelength shift, whereby laser radiation having a predetermined wavelength related to the wavelength of said laser source directed toward the center of the eye is diffracted away from the eye in a direction that is not retroreflective for all angles of incidence.

17. The method of providing laser eye protection claimed in claim 16, wherein:
said step of exposing said photosensitive layer (step(c)) includes the steps of
(i) forming a light beam having a long coherence length relative to the thickness of the photosensitive layer; and
(ii) limiting the coherence length of said light beam to a length adequate for forming interference fringes within the photosensitive layer without forming any secondary interference fringes that would result from the interference of light beams reflected from the inner surface of the supporting substrate with light beams traveling directly to the photosensitive layer from said laser source.

18. The method of providing laser eye protection claimed in claim 16, wherein:
said step of disposing said holographic optical element before the eye of a user (step(e)) by locating the center of the eye at a position relative to said holographic optical element differing from the position of said exposure point relative to said photosensitive layer during exposure of said photosensitive layer in a manner dependent upon the relationship between said predetermined wavelength and the wavelength of the laser source.

19. The method of providing laser eye protection claimed in claim 16, wherein:
said step of developing said exposed photosensitive layer (step(d)) includes changing the thickness of said photosensitive layer thereby changing the spacing of said interference fringes, whereby said predetermined wavelength differs from the wavelength of said laser point source by a factor dependent upon the ratio of the change in thickness of said photosensitive layer during development.

20. The method of providing laser eye protection claimed in claim 16, wherein:
said step of developing said photosensitive layer (step(d)) preserves the thickness of said photosensitive layer;
said step of disposing said holographic optical element before the eye of a user (step(e)) by locating the center of the eye at a position relative to the holographic optical element substantially the same as the position of said exposure point relative to the photosensitive layer during exposure of said photosensitive layer, whereby said predetermined wavelength is equal to the wavelength of said laser source.

21. The method of providing laser eye protection claimed in claim 16, wherein:
said photosensitive layer consists of dichromated gelatin.

22. The method of providing laser eye protection comprising the steps of:
(a) forming a first photosensitive layer on the outer surface of a first curved transparent supporting substrate having a corresponding first approximate center of curvature;
(b) disposing a first reflecting surface conformal to the outer surface of said first photosensitive layer for reflecting light inward from said first curved transparent supporting substrate, said first reflecting surface thereby having a corresponding first approximate center of curvature;
(c) exposing said first photosensitive layer with a first exposure source having an area of minimum cross section located at a first exposure point, said first exposure point located a distance closer to said first reflecting surface than said first approximate center of curvature of said first reflecting surface, thereby causing first interference fringes in said first photosensitive layer from the interference of light directly from said first exposure source and light reflected from said first reflecting surface;
(d) removing said first reflecting surface from said first photosensitive layer;
(e) developing said exposed first photosensitive layer to form a first holographic optical element including said first interference fringes;
(f) forming a second photosensitive layer on the outer surface of a second curved transparent supporting substrate having a corresponding second approximate center of curvature, said second transparent supporting substrate being conformal to the shape of said first photosensitive layer;

(g) disposing a second reflecting surface conformal to the outer surface of said second photosensitive layer for reflecting light inward from said second curved transparent supporting substrate, said second reflecting surface thereby having a corresponding second approximate center of curvature;

(h) exposing said second photosensitive layer with a second exposure source having an area of minimum cross section located at a second exposure point, said second exposure point located a distance closer to said second reflecting surface than said second approximate center of curvature of said second reflecting surface, thereby causing second interference fringes in said second photosensitive layer from the interference of light directly from said second exposure source and light reflected from said second reflecting surface;

(i) removing said second reflecting surface from said second photosensitive layer;

(j) developing said second photosensitive layer to form a second holographic optical element including said second interference fringes; and (k) disposing said first and second holographic optical elements before the eyes of a user in tandem whereby the center of a first eye is located in a position relative to said first holographic optical element having a predetermined relationship to the position of said first exposure point relative to said first photosensitive layer during exposure of said first photosensitive layer for wavelength shift and the center of a second eye is located in a position relative to said second holographic element having a predetermined relationship to the position of said second exposure point relative to said photosensitive layer during exposure of said second photosensitive layer for wavelength shift, whereby laser radiation having a predetermined wavelength related to the wavelength of said first and second laser sources directed toward the center of either eye is diffracted away from that eye in a direction that is not retroreflective for all angles of incidence.

23. The method of providing laser eye protection claimed in claim 22, wherein:

said steps of exposing said first and second photosensitive layers (step(c)) each include the steps of (i) forming respective first and second light beams each having a long coherence length relative to the thickness of the corresponding photosensitive layer; and (ii) limiting the coherence length of said light beam to a length adequate for forming interference fringes within the photosensitive layer without forming any secondary interference fringes that would result from the interference of light beams reflected from the inner surface of the supporting substrate with light beams traveling directly to the photosensitive layer from said laser source.

24. The method of providing laser eye protection comprising the steps of:

(a) forming a first photosensitive layer on the outer surface of a first curved transparent supporting substrate, an outer surface of said first photosensitive layer thereby having a corresponding first approximate center of curvature;

(b) disposing atmospheric air beyond the outer surface of said first photosensitive layer;

(c) exposing said first photosensitive layer with a first exposure source having an area of minimum cross section located at a first exposure point, said first exposure point located a distance closer to the outer surface of said first photosensitive layer than said first approximate center of curvature, thereby causing first interference fringes in said first photosensitive layer from the interference of light directly from said first exposure source and light reflected from the outer surface of said first photosensitive layer due to the difference in index of refraction between said first photosensitive layer and atmospheric air;

(d) developing said exposed first photosensitive layer to form a first holographic optical element including said first interference fringes;

(e) forming a second photosensitive layer on the outer surface of a second curved transparent supporting substrate, an outer surface of said second photosensitive layer thereby having a corresponding second approximate center of curvature, said second transparent supporting substrate being conformal to the shape of said first photosensitive layer;

(f) disposing atmospheric air beyond the outer surface of said second photosensitive layer;

(g) exposing said second photosensitive layer with a second exposure source having an area of minimum cross section located at a second exposure point, said second exposure point located a distance closer to the outer surface of said second photosensitive layer than said second approximate center of curvature, thereby causing second interference fringes in said second photosensitive layer from the interference of light directly from said second exposure source and light reflected from the outer surface of said second photosensitive layer due to the difference in index of refraction between said second photosensitive layer and atmospheric air;

(h) developing said second photosensitive layer to form a second holographic optical element including said second interference fringes; and (i) disposing said first and second holographic optical elements before the eyes of a user in tandem whereby the center of a first eye is located in a position relative to said first holographic optical element having a predetermined relationship to the position of said first exposure point relative to said first photosensitive layer during exposure of said first photosensitive layer for wavelength shift and the center of a second eye is located in a position relative to said second holographic element having a predetermined relationship to the position of said second exposure point relative to said photosensitive layer during exposure of said second photosensitive layer for wavelength shift, whereby laser radiation having a predetermined wavelength related to the wavelength of said first and second laser sources directed toward the center of either eye is diffracted away from that eye in a direction that is not retroreflective for all angles of incidence.

25. The method of providing laser eye protection claimed in claim 24, wherein:

said step of exposing said first and second photosensitive layers (step(c)) includes the steps of (i) forming respective first and second light beams having a long coherence length relative to the thickness of the corresponding photosensitive layer; and (ii) limiting the coherence length of said light beam to a length adequate for forming interference fringes within the photosensitive layer without forming any secondary interference fringes that would result from the interference of light beams reflected from the inner surface of the supporting substrate with light beams traveling directly to the photosensitive layer from said laser source.

26. A method of providing laser eye protection comprising the steps of:
  (a) forming a photosensitive layer on the outer surface of a curved transparent supporting substrate;
  (b) disposing a reflecting surface conformal to the outer surface of said photosensitive layer for reflecting light inward from said curved transparent supporting substrate, said reflecting surface thereby having an approximate center of curvature;
  (c) exposing said photosensitive layer with two exposure sources, each having an area of minimum cross section located at respective first and second exposure points, thereby causing a first set of interference fringes in said photosensitive layer from the interference of light directly from said first exposure source and light from said first exposure source reflected from said reflecting surface and a second set of interference fringes in said photosensitive layer from the interference of light directly from said second exposure source and from light said second exposure source reflected from said reflecting surface;
  (d) removing said reflecting surface from said photosensitive layer;
  (e) developing said exposed photosensitive layer to form a holographic optical element including said first and second sets of interference fringes; and
  (f) disposing said holographic optical element before the eyes of a user whereby the center of each eye is located at a position relative to the holographic optical element having a predetermined relationship to the position of a corresponding one of said exposure points relative to said photosensitive layer during exposure of said photosensitive layer for wavelength shift, whereby laser radiation having a predetermined wavelength related to the wavelength of the corresponding laser source directed toward the center of either eye is diffracted away from the eye in a direction that is not retroreflective for all angles of incidence.

27. The method of providing laser eye protection claimed in claim 26, wherein:
  said step of exposing said photosensitive layer with two exposure sources (step(c)) includes the steps of
  (i) forming respective light beams having a long coherence length relative to the thickness of the photosensitive layer; and
  (ii) limiting the coherence length of said light beam to a length adequate for forming interference fringes within the photosensitive layer without forming any secondary interference fringes that would result from the interference of light beams reflected from the inner surface of the supporting substrate with light beams traveling directly to the photosensitive layer from said laser source.

28. The method of providing laser eye protection claimed in claim 26, wherein:
  said step of exposing said photosensitive layer with two exposure sources (step(c)) includes simultaneous exposure of said photosensitive layer to said two exposure sources.

29. The method of providing laser eye protection claimed in claim 26, wherein:
  said step of exposing said photosensitive layer with two laser sources (step(c)) includes sequential exposure of said photosensitive layer to a first exposure source and then to a second exposure source.

30. The method of providing laser eye protection claimed in claim 26, wherein:
  said step of exposing said photosensitive layer with two exposure sources having areas of minimum cross section at respective first and second exposure points (step(c)) includes sequentially
  (i) disposing said photosensitive layer relative to a single exposure source whereby said area of minimum cross section is at said first exposure point;
  (ii) exposing said photosensitive layer with said single exposure source;
  (iii) displacing said photosensitive layer relative to said single exposure source whereby said area of minimum cross section is at said second exposure point; and
  (iv) exposing said photosensitive layer with said single exposure source.

31. A method of providing laser eye protection comprising the steps of:
  (a) forming a photosensitive layer on the outer surface of a curved transparent supporting substrate, an outer surface of said photosensitive layer thereby having an approximate center of curvature;
  (b) disposing atmospheric air beyond the outer surface of said photosensitive layer;
  (c) exposing said photosensitive layer with two exposure sources, each having an area of minimum cross section located at respective first and second exposure points, said first and second exposure points each located a distance closer to the outer surface of said photosensitive layer than said approximate center of curvature, thereby causing a first set of interference fringes in said photosensitive layer from the interference of light directly from said first exposure source and light from said first exposure source reflected from the outer surface of said photosensitive layer due to the difference in index of refraction between said photosensitive layer and atmospheric air and a second set of interference fringes in said photosensitive layer from the interference of light directly from said second exposure source and light from said second exposure source reflected from the outer surface of said photosensitive layer due to the difference in index of refraction between said photosensitive layer and atmospheric air;
  (d) developing said exposure photosensitive layer to form a holographic optical element including said first and second sets of interference fringes; and
  (e) disposing said holographic optical element before the eyes of a user whereby the center of each eye is located at a position relative to the holographic optical element having a predetermined relationship to the position of a corresponding one of said exposure points relative to said photosensitive layer during exposure of said photosensitive layer for wavelength shift, whereby laser radiation having a predetermiend wavelength related to the wavelength of the corresponding laser source directed toward the center of either eye is diffracted away from that eye in a direction that is not retro-reflective for all angles of indicence.

32. The method of providing laser eye protection claimed in claim 31, wherein:
said step of exposing and photosensitive layer with two exposure sources (step(c)) includes the steps of
(i) forming respective light beams having a long coherence length relative to the thickness of said photosensitive layer; and
(ii) limiting the coherence length of said light beam to a length adequate for forming interference fringes within the photosensitive layer without forming any secondary interference fringes that would result from the interference of light beams reflected from the inner surface of the supporting substrate with light beams traveling directly to the photosensitive layer from said laser source.

33. The method of providing laser eye protection claimed in claim 31, wherein:
said step of exposing said photosensitive layer with two exposure sources (step(c)) includes simultaneous exposure of said photosensitive layer to said two exposure sources.

34. The method of providing laser eye protection claimed in claim 31, wherein:
said step of exposing said photosensitive layer with two exposure sources (step(c)) includes sequential exposure of said photosensitive layer to a first exposure source and then to a second exposure source.

35. The method of providing laser eye protection claimed in claim 31, wherein:
said step of exposing said photosensitive layer with two exposure sources having areas of minimum cross section at respective first and second exposure points (step(c)) includes sequentially
(i) disposing said photosensitive layer relative to a single exposure source whereby said area of minimum cross section is at said first exposure point;
(ii) exposing said photosensitive layer with said single exposure source;
(iii) displacing said photosensitive layer relative to said single exposure source whereby said area of minumum cross section is at said second exposure point; and
(iv) exposing said photosensitive layer with said single exposure source.

36. A method of providing laser eye protection against laser radiation of a plurality of wavelengths comprising the steps of:
(a) forming a photosensitive layer on the outer surface of a curved transparent supporting substrate;
(b) disposing a reflecting surface conformal to the outer surface of said photosensitive layer for reflecting light inward from said first curved transparent supporting substrate, said reflecting surface thereby having an approximate center of curvature;
(c) exposing said photosensitive layer with a plurality of exposure sources equal in number to the plurality of wavelengths of laser radiation, each exposure source having an area of minimum cross section located at a corresponding exposure point, each exposure point located a distance closer to said reflecting surface than said approximate center of curvature of said reflective surface, thereby causing a plurality of sets of interference fringes in said photosensitive layer, each set of interference fringes from the interference of light reaching said photosensitive layer directly from a corresponding exposure source and light from the same exposure source reflected from said reflecting surface;
(d) removing said reflecting surface from said photosensitive layer;
(e) developing said photosensitive layer to form a holographic optical element including said plurality of sets of interference fringes; and
(f) disposing said holographic optical element before an eye of a user, whereby the center of the eye is located at a position relative to the holographic optical element having a predetermined relationship to the position of each of the corresponding exposure points relative to said photosensitive layer during exposure of said photosensitive layer for wavelength shift, whereby laser radiation having one of said plurality of wavelengths directed to the center of the eye is diffracted away from the eye by a corresponding set of interference fringes in a direction that is not retroreflective for all angles of incidence.

37. The method of providing laser eye protection claimed in claim 36, wherein:
said step of exposing said photosensitive layer with a plurality of exposure sources (step(c)) each includes the steps of
(i) forming a light beam having a long coherence length relative to the thickness of said photosensitive layer; and
(ii) limiting the coherence length of said light beam to a length adequate for forming interference fringes within the photosensitive layer without forming any secondary interference fringes that would result from the interference of light beams reflected from the inner surface of the supporting substrate with light beams traveling directly to the photosensitive layer from said laser source.

38. The method of providing laser eye protection claimed in claim 36, wherein:
said step of exposing said photosensitive layer with a plurality of exposure sources (step(c)) includes simultaneous exposure of said photosensitive layer to said plurality of exposure sources.

39. The method of providing laser eye protection claimed in claim 36, wherein:
said step of exposing said photosensitive layer with a plurality of exposure sources (step(c)) includes sequential exposure of said photosensitive layer to said plurality of exposure sources.

40. The method of providing laser eye protection claimed in claim 36, wherein:
said step of exposing said photosensitive layer with a plurality of exposure sources having areas of minimum cross section at respective exposure points (step (c)) includes repeatedly
(i) disposing said photosensitive layer relative to a single exposure source whereby said area of minimum cross section is at a corresponding one of said exposure points; and
(ii) exposing said photosensitive layer with said single exposure source.

41. A method of providing laser eye protection against laser radiation at a plurality of wavelengths comprising the steps of:

(a) forming a photosensitive layer on the outer surface of each of a plurality of curved transparent supporting substrates, each curved transparent supporting substrate having a corresponding approximate center of curvature said plurality of curved transparent supporting substrates forming a sequence whereby each curved transparent supporting substrate other than a first curved transparent supporting substrate is conformal to the shape of the photosensitive layer formed on a previous curved transparent supporting substrate;

(b) disposing a corresponding reflecting surface conformal to the outer surface of each said photosensitive layers for reflecting light inward from said corresponding curved transparent supporting substrate, each reflecting surface thereby having a corresponding approximate center of curvature;

(c) exposing each of said photosensitive layers with a corresponding exposure source having an area of minimum cross section located at a corresponding exposure point, each exposure point located a distance closer to said corresponding
reflecting surface than said corresponding approximate center of curvature of said reflectin su, thereby causing interference fringes in said corresponding photosensitive layer from the interference of light reaching said corresponding photosensitive layer directly from said exposure source and light reflected from the corresponding reflective surface;

(d) removing said reflecting surface from each of said photosensitive layers;

(e) developing each exposed photosensitive layer to form a corresponding holographic optical element including corresponding interference fringes; and (f) disposing the plurality of holographic optical elements before an eye of a user in tandem, whereby the center of the eye is located at a position relative to the corresponding holographic optical element having a predetermined relationship to the position of each of the corresponding exposure points relative to said corresponding photosensitive layer during exposure of said corresponding photosensitive layer for wavelength shift, whereby laser radiation having one of said plurality of wavelengths directed to the center of the eye is diffracted away from the eye by a corresponding holographic optical element in a direction that is not retroreflective for all angles of incidence.

42. The method of providing laser eye protection claimed in claim 41, wherein:

said steps of exposing said plurality of photosensitive layers (step(c)) each includes the steps of (i) forming respective light beams each having a long coherence length relative to the thickness of said corresponding photosensitive layer; and (ii) limiting the coherence length of said light beam to a length adequate for forming interference fringes within the photosensitive layer without forming any secondary interference fringes that would result from the interference of light beams reflected from the inner surface of the supporting substrate with light beams traveling directly to the photosensitive layer from said laser source.

43. A method of providing laser eye protection against laser radiation at a plurality of wavelengths comprising the steps of:

(a) forming a photosensitive layer on the outer surface of a curved transparent supporting substrate an outer surface of said photosensitive layer thereby having an approximate center of curvature;

(b) disposing atmospheric air beyond the outer surface of said photosensitive layer;

(c) exposing said photosensitive layer with a plurality of exposure sources equal in number to the plurality of wavelengths of laser radiation, each exposure source having an area of minimum cross section located at a corresponding exposure point, each exposure point located a distance closer to the outer surface of said photosensitive layer than said approximate center of curvature, thereby causing a plurality of sets of interference fringes in said photosensitive layer, each set of interference fringes from the interference of light directly from a corresponding exposure source and light from the same exposure source reflected from said reflecting surface;

(d) developing said photosensitive layer to form a holographic optical element including said plurality of sets of interference fringes; and (e) disposing said holographic optical element before an eye of a user, whereby the center of the eye is located at a position relative to the holographic optical element having a predetermined relationship to the position of each of the corresponding exposure points relative to said photosensitive layer during exposure of said photosensitive layer for wavelength shift, whereby laser radiation having one of said plurality of wavelengths directed to the center of the eye is diffracted away from the eye by a corresponding set of interference fringes in a direction that is not retroreflective for all angles of incidence.

44. The method of providing laser eye protection claimed in claim 43, wherein:

said step of exposing said photosensitive layer with a plurality of exposure sources (step(c)) includes the steps of (i) forming respective light beams having a long coherence length relative to the thickness of said photosensitive layer; and (ii) limiting the coherence length of said light beam to a length adequate for forming interference fringes within the photosensitive layer without forming any secondary interference fringes that would result from the interference of light beams reflected from the inner surface of the supporting substrate with light beams traveling directly to the photosensitive layer from said laser source.

45. The method of providing laser eye protection claimed in claim 43, wherein:

said step of exposing said photosensitive layer with a plurality of exposure sources (step(c)) includes simultaneous exposure of said photosensitive layer to said plurality of exposure sources.

46. The method of providing laser eye protection claimed in claim 43, wherein:

said step of exposing said photosensitive layer with a plurality of exposure sources (step(c)) includes sequential exposure of said photosensitive layer to said plurality of exposure sources.

47. The method of providing laser eye protection claimed in claim 43, wherein:
said step of exposing said photosensitive layer with a plurality of exposure sources having areas of minimum cross section at respective exposure points (step(c)) includes repeatedly
(i) disposing said photosensitive layer relative to a single exposure source whereby said area of minimum cross section is at a corresponding one of said exposure points; and
(ii) exposing said photosensitive layer with said single exposure source.

48. A method of providing laser eye protection against laser radiation at a plurality of wavelengths comprising the steps of:
(a) forming a photosensitive layer on the outer surface of each of a plurality of curved transparent supporting substrates, each photosensitive layer thereby having a corresponding approximate center of curvature, said plurality of curved transparent supporting substrates formed in a sequence whereby each curved transparent supporting substrate other than a first curved transparent supporting substrate is conformal to the shape of the photosensitive layer formed on a previous curved transparent supporting substrate;
(b) disposing atmospheric air beyond the outer surface of each of said photosensitive layers;
(c) exposing each of said photosensitive layers with a corresponding exposure source having an area of minimum cross section located at a corresponding exposure point, each exposure point located a distance closer to
the outer surface of said corresponding photosensitive layer than said corresponding approximate center of curvature, thereby causing interference fringes in said corresponding photosensitive layer from the interference of light directly from said corresponding exposure source and light from said corresponding exposure source reflected from the outer surface of the corresponding photosensitive layer due to the difference in index of refraction between said corresponding photosensitive layer and atmospheric air;
(d) developing each exposed photosensitive layer to form a correpsonding holographic optical element including corresponding interference fringes; and
(e) disposing the plurality of holographic optical elements before an eye of a user in tandem, whereby the center of the eye is located at a position relative to the corresponding holographic optical element having a predetermined relationship to the position of each of the corresponding exposure points relative to said corresponding photosensitive layer during exposure of said corresponding photosensitive layer for wavelength shift, whereby laser radiation having one of said plurality of wavelengths directed to the center of the eye is diffracted away from the eye by a corresponding holographic optical element in a direction that is not retroreflective for all angles of incidence.

49. The method of providing laser eye protection claimed in claim 48, wherein:
said step of exposing each photosensitive layer (step(c)) includes the steps of
(i) forming respective light beams having a long coherence length relative to the thickness of the corresponding photosensitive layer; and
(ii) limiting the coherence length of said light beam to a length adequate for forming interference fringes within the photosensitive layer without forming any secondary interference fringes that would result from the interference of light beams reflected from the inner surface of the supporting substrate with light beams traveling directly to the photosensitive layer from said laser source.

* * * * *

UNITED STATES PATENT AND TRADEMARK OFFICE
CERTIFICATE OF CORRECTION

PATENT NO. : 4,830,441
DATED : May 16, 1989
INVENTOR(S) : Chang

It is certified that error appears in the above-identified patent and that said Letters Patent is hereby corrected as shown below:

Column 1, line 3, "EYEWEAR1" should be --EYEWEAR--.

Column 21, line 15, "substrate;" should be --substrate having an approximate center of curvature;--.

Column 23, line 57, "substrate;" should be --substrate having an approximate center of curvature;--.

Column 25, line 27, "reflectin su" should be --reflecting surface--.

Signed and Sealed this

Sixth Day of March, 1990

*Attest:*

JEFFREY M. SAMUELS

*Attesting Officer*     *Acting Commissioner of Patents and Trademarks*